(12) United States Patent
Hernandez-Guerra

(10) Patent No.: US 6,687,330 B2
(45) Date of Patent: Feb. 3, 2004

(54) SYSTEM AND METHOD FOR INTENSITY MODULATED RADIATION THERAPY

(75) Inventor: Francisco M. Hernandez-Guerra, Concord, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 316 days.

(21) Appl. No.: 09/918,879

(22) Filed: Jul. 31, 2001

(65) Prior Publication Data

US 2003/0026384 A1 Feb. 6, 2003

(51) Int. Cl.⁷ .................................................. A61N 5/10
(52) U.S. Cl. ......................................................... 378/65
(58) Field of Search ........................................... 378/65

(56) References Cited

U.S. PATENT DOCUMENTS

| | | | |
|---|---|---|---|
| 5,148,032 A | 9/1992 | Hernandez | 250/492.1 |
| 5,724,403 A | 3/1998 | Siochi et al. | 378/150 |
| 5,764,723 A * | 6/1998 | Weinberger et al. | 378/65 |
| 5,818,902 A | 10/1998 | Yu | 378/65 |
| 6,052,430 A | 4/2000 | Siochi et al. | 378/65 |
| 6,134,296 A | 10/2000 | Siochi | 378/65 |
| 6,208,712 B1 | 3/2001 | Hernandez-Guerra | 378/150 |
| 6,240,162 B1 * | 5/2001 | Hernandez-Guerra et al. | 378/65 |

OTHER PUBLICATIONS

Compatibility of Varian 2100C gated operations with enhanced dynamic wedge and IMRT dose delivery, Med. Phys., Aug. 2000.

* cited by examiner

Primary Examiner—David V. Bruce
Assistant Examiner—Jurie Yun

(57) ABSTRACT

A dynamic IMRT scheme. A RAD ON/RAD OFF cycle is an IMRT segment. Every set of opposing leaves in the collimator produces an IMRT profile or track. According to such an embodiment, at least one of the opposing leaves moves toward the other to produce the given track. When a track is complete, the opposing leaves remain together until the end of the segment. The dose rate remains constant during the segment.

12 Claims, 10 Drawing Sheets

| time(sec) | | | | | | | | | | time(sec) |
|---|---|---|---|---|---|---|---|---|---|---|
| | 1b | | | 20.00 | 20.00 | 20.00 | 20.00 | 20.00 | < | 1a | 2.5 |
| | 2b | | | 4.00 | 10.00 | 6.67 | 20.00 | < | | 2a | 5.5 |
| | 3b | | 0.80 | 1.00 | 1.33 | 4.00 | 4.00 | 20.00 | < | 3a | 35.5 |
| | 4b | | 0.57 | 1.00 | 1.33 | 4.00 | 1.82 | < | | 4a | 43 |
| | 5b | | 0.50 | 1.00 | 1.00 | 2.50 | 1.54 | < | | 5a | 50.5 |
| | 6b | | 0.67 | 0.80 | 1.00 | 1.67 | 1.43 | < | | 6a | 50.5 |
| | 7b | | 0.80 | 0.80 | 1.54 | 1.18 | 1.82 | < | | 7a | 45.5 |
| | 8b | | 0.67 | 0.80 | 2.00 | 1.67 | 2.22 | < | | 8a | 43 |
| | 9b | | 0.80 | 0.80 | 1.00 | 2.00 | 2.50 | 2.86 | 20.00 | < | 9a | 35.5 |
| | 10b | | | 1.33 | 10.00 | 6.67 | 5.00 | 10.00 | < | 10a | 13 |
| 2.5 | 11b | | | -10.00 | -6.67 | 4.00 | 20.00 | < | | 11a | 3 |
| | 12b | | | | 20.00 | 20.00 | 20.00 | < | | 12a | 1.5 |

Fluence

MLC Shape

Head&Neck Intensity Map Example

- One possible solution composed of two IMRT Segments

FIG. 8A

Legend:
- 100-120
- 80-100
- 60-80
- 40-60
- 20-40
- 0-20

| Field → | a | b | c | d | e | f | g | h | i | |
|---|---|---|---|---|---|---|---|---|---|---|
| 0b / 0a | 0 | 0 | 0 | 0 | 0 | 0 | 0 | 0 | 0 | |
| 1b / 1a | 0 | 0 | 0 | 0 | 0 | 0 | 0 | 0 | 0 | |
| 2b / 2a | 0 | 0 | 24 | 23 | 22 | 21 | 20 | 30 | 0 | |
| 3b / 3a | 0 | 90 | 30 | 25 | 23 | 20 | 22 | 40 | 0 | |
| 4b / 4a | 0 | 105 | 65 | 45 | 30 | 25 | 20 | 80 | 0 | |
| 5b / 5a | 0 | 120 | 70 | 50 | 35 | 30 | 40 | 20 | 0 | |
| 6b / 6a | 0 | 120 | 80 | 60 | 40 | 32 | 0 | 0 | 0 | |
| 7b / 7a | 0 | 110 | 90 | 65 | 45 | 33 | 0 | 0 | 0 | |
| 8b / 8a | 0 | 105 | 85 | 60 | 47 | 30 | 0 | 20 | 0 | 802 |
| 9b / 9a | 0 | 90 | 75 | 50 | 40 | 28 | 20 | 60 | 0 | |
| 10b / 10a | 0 | 0 | 65 | 45 | 35 | 27 | 21 | 40 | 0 | |
| 11b / 11a | 0 | 0 | 45 | 30 | 28 | 25 | 22 | 30 | 0 | 804 |
| 12b / 12a | 0 | 0 | 20 | 22 | 25 | 20 | 20 | 0 | 0 | |
| 13b / 13a | 0 | 0 | 0 | 0 | 22 | 21 | 0 | 0 | 0 | |

Leaves

| | | | | | | | |
|---|---|---|---|---|---|---|---|
| 1b  |       | 5.00   |       | 3.00  | 2.00  |      | 1a  |
| 2b  |       | 11.00  | 4.00  | 4.00  | 1.00  |      | 2a  |
| 3b  | 71.00 | 46.00  | 6.00  | 11.00 | 6.00  | 1.00 | 3a  |
| 4b  | 86.00 | 51.00  | 26.00 | 16.00 | 11.00 |      | 4a  |
| 5b  | 101.00| 61.00  | 31.00 | 21.00 | 13.00 | 1.00 | 5a  |
| 6b  | 101.00| 71.00  | 41.00 | 26.00 | 14.00 |      | 6a  |
| 7b  | 91.00 | 66.00  | 46.00 | 28.00 | 11.00 |      | 7a  |
| 8b  | 86.00 | 56.00  | 41.00 | 21.00 | 9.00  |      | 8a  |
| 9b  | 71.00 | 46.00  | 31.00 | 16.00 | 8.00  | 1.00 | 9a  |
| 10b |       | 26.00  | 26.00 | 9.00  | 6.00  | 2.00 | 10a |
| 11b |       | 1.00   | 11.00 | 6.00  | 1.00  |      | 11a |
| 12b |       |        | 3.00  | 3.00  | 2.00  | 1.00 | 12a |

| time(sec) | | | | | | | | | time(sec) |
|---|---|---|---|---|---|---|---|---|---|
| 1b  |      | 20.00  | 20.00 | 20.00 | 20.00 | 20.00 |   | 1a  | 2.5  |
| 2b  | 0.80 | 4.00   | 10.00 | 6.67  | 20.00 | 20.00 |   | 2a  | 5.5  |
| 3b  | 0.57 | 1.00   | 1.33  | 4.00  | 4.00  | <     | < | 3a  | 35.5 |
| 4b  | 0.50 | 1.00   | 1.33  | 4.00  | 1.82  | 20.00 |   | 4a  | 43   |
| 5b  | 0.67 | 1.00   | 1.00  | 2.50  | 1.54  | <     | < | 5a  | 50.5 |
| 6b  | 0.80 | 0.80   | 1.00  | 1.67  | 1.43  | <     | < | 6a  | 50.5 |
| 7b  | 0.67 | 0.80   | 1.54  | 1.18  | 1.82  | <     | < | 7a  | 45.5 |
| 8b  | 0.80 | 0.80   | 2.00  | 1.67  | 2.22  | <     |   | 8a  | 43   |
| 9b  |      | 0.80   | 2.00  | 2.50  | 2.86  | 20.00 | < | 9a  | 35.5 |
| 10b |      | 1.33   | 10.00 | 6.67  | 5.00  | 10.00 | < | 10a | 13   |
| 11b |      | -10.00 | -6.67 | 4.00  | 20.00 | 20.00 |   | 11a | 3    |
| 12b | 2.5  |        |       | 20.00 | 20.00 | 20.00 | < | 12a | 1.5  |

| | 1a | 2a | 3a | 4a | 5a | 6a | 7a | 8a | 9a | 10a | 11a | 12a |
|---|---|---|---|---|---|---|---|---|---|---|---|---|
| | | 3.00 | 11.00 | 21.00 | 61.00 | 1.00 | 1.00 | 41.00 | 21.00 | 3.00 | | |
| | | | | 21.00 | | | | | | 11.00 | | |
| 1b | 2b | 3b | 4b | 5b | 6b | 7b | 8b | 9b | 10b | 11b | 12b | |

FIG. 12

| | 1a | 2a | 3a | 4a | 5a | 6a | 7a | 8a | 9a | 10a | 11a | 12a |
|---|---|---|---|---|---|---|---|---|---|---|---|---|
| | | 6.67 | 2.50 | 0.95 | 0.50 | > | > | 20.00 | 0.49 | 0.95 | 2.50 | |
| | | > | | > | 20.00 | | | > | > | > | 6.67 | |
| time(sec) | 5.5 | 10.5 | 30.5 | 0.5 | | | | 0.5 | 20.5 | 10.5 | 5.5 | |
| | 1b | 2b | 3b | 4b | 5b | 6b | 7b | 8b | 9b | 10b | 11b | 12b |

SYSTEM AND METHOD FOR INTENSITY MODULATED RADIATION THERAPY

BACKGROUND OF THE INVENTION

The present invention relates to radiation therapy, and more particularly, to a system and method for efficiently delivering radiation treatment.

DESCRIPTION OF THE RELATED ART

Radiation emitting devices are generally known and used, for instance, as radiation therapy devices for the treatment of patients. A radiation therapy device generally includes a gantry which can be swiveled around a horizontal axis of rotation in the course of a therapeutic treatment. A linear accelerator is located in the gantry for generating a high energy radiation beam for therapy. This high energy radiation beam can be an electron beam or photon (X-ray) beam. During treatment, this radiation beam is trained on one zone of a patient lying in the isocenter of the gantry rotation.

To control the radiation emitted toward an object, a beam shielding device, such as a plate arrangement or a collimator, is typically provided in the trajectory of the radiation beam between the radiation source and the object. An example of a plate arrangement is a set of four plates that can be used to define an opening for the radiation beam. A collimator is a beam shielding device which could include multiple leaves, for example, a plurality of relatively thin plates or rods, typically arranged as opposing leaf pairs. The plates themselves are formed of a relatively dense and radiation impervious material and are generally independently positionable to delimit the radiation beam.

The beam shielding device defines a field on the object to which a prescribed amount of radiation is to be delivered. The usual treatment field shape results in a three-dimensional treatment volume which includes segments of normal tissue, thereby limiting the dose that can be given to the tumor. The dose delivered to the tumor can be increased if the amount of normal tissue being irradiated is decreased and the dose delivered to the normal tissue is decreased. Avoidance of delivery of radiation to the organs surrounding and overlying the tumor determines the dosage that can be delivered to the tumor.

Typical radiation therapy machines deliver treatment in the form of "intensity modulated radiation therapy." Essentially, multiple coplanar beams whose fluence profiles are modulated in two dimensions are used to achieve a uniform high dose region that closely conforms to a target volume in three dimensions and thus spares normal tissue regions.

For example, FIG. 1A and FIG. 1B illustrate a discrete intensity map 100 having a footprint 102 that is to be delivered in treatment.

The direction X denotes a dose level to be applied. FIG. 1A illustrates the intensity map; FIG. 1B illustrates the map applied on the patient 104.

In general, IMRT may be delivered in any of three ways: static IMRT (also known as "Step and Shoot"); Dynamic IMRT (also known as "sliding window"); and IMAT (arc IMRT).

FIG. 2A and FIG. 2B illustrate static or sequential IMRT. In particular, shown are a multi-leaf collimator 200 defining a shape 204 and an associated fluence profile 203. As shown, the leaves 202a, 202b of the MLC 200 define an opening 204 that is to be delivered. Radiation is on for a predetermined period while the leaf settings are as shown. The particular leaf setting 204 corresponds to a step of the fluence profile. Thus, the fluence profile consists of a plurality of such settings built up in a stepwise fashion.

FIG. 3 illustrates sliding window IMRT. Shown at 302 is a track or "side view" of the intensity map, for a given set of two opposing collimator leaves. In dynamic IMRT, radiation is ON while the leaves are moving. Thus, shown in 303 is a diagram of a particular leaf motion corresponding to the map 302 over time. The leaf assumes various positions 304a ... 304n over time, and defines various openings 306a ... 306n correspondingly. Thus, each level 308a, 308b, 308c and so on is built over time, with the peaks 310, 312 being built separately.

In this technique, a variable width slot moves across the field and exposes every point on the intensity map to create slopes. At both the beginning and ending of the treatment, the collimator is closed. The leaves are closed simultaneously as the radiation is turned off. This can result in delivery of excess radiation, if the closing of the leaf and the turning off of the radiation are not synchronized.

Finally, in arc IMRT, the radiation stays on while the leaves are moving and the gantry is rotating at constant speed. While using this technique, one intensity level is delivered per gantry revolution.

SUMMARY OF THE INVENTION

These and other problems in the prior art are overcome in large part by a system and method for control of radiation therapy delivery according to the present invention.

A dynamic IMRT scheme according to an embodiment of the invention defines a RAD ON/RAD OFF cycle as an IMRT segment. Every set of opposing leaves in the collimator produces an IMRT profile or track. According to such an embodiment, at least one of the opposing leaves moves toward the other to produce the given track. When a track is complete, the opposing leaves remain together until the end of the segment. The dose rate remains constant during the segment.

BRIEF DESCRIPTION OF THE DRAWINGS

A better understanding of the present invention can be obtained when the following detailed description is considered in conjunction with the following drawings in which:

FIG. 8A and FIG. 8B illustrate an example intensity map;

FIG. 9 and FIG. 10 illustrate delivery of a first segment of the intensity map of FIG. 8; and FIG. 11 and FIG. 12 illustrate delivery of a second segment of the intensity map of FIG. 8.

DETAILED DESCRIPTION OF THE INVENTION

FIGS. 4–12 illustrate a system and method for intensity modulated radiation therapy according to embodiments of the present invention.

Figure 4:
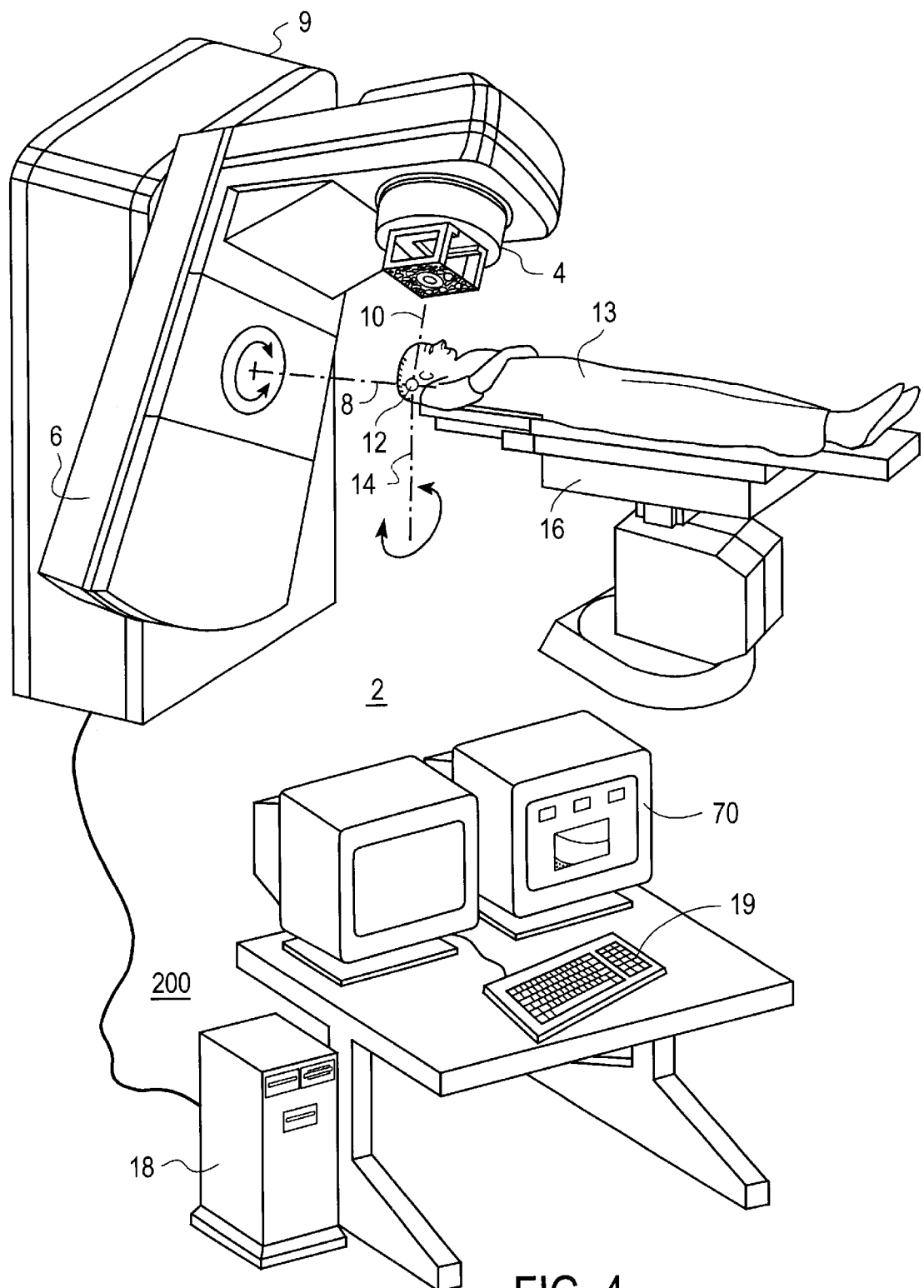
FIG. 4 illustrates an exemplary radiation therapy system according to an implementation of the invention.

Turning now to the drawings and, with particular attention to FIG. 4, a radiation treatment apparatus embodying the present invention is shown therein and generally identified by reference numeral 2. The radiation therapy apparatus 2 may be a Mevatron or Primus linear accelerator available from Siemens Medical Systems. The radiation treatment apparatus 2 includes a beam shielding device (not shown) within a treatment head 4, a control unit in a housing 9 and a treatment unit 200 according to the present invention. The radiation treatment device 2 includes a gantry 6 which can be swiveled around a horizontal axis of rotation 8 in the course of a therapeutic treatment. The treatment head 4 is fastened to a projection of the gantry 6. A linear accelerator is located in the gantry 6 to generate the high powered radiation required for the therapy. The axis of the radiation bundle emitted from the linear accelerator and the gantry 6 is designated by 10. Electron, photon or any other detectable radiation can be used for the therapy.

During the treatment, the radiation beam is trained on a zone 12 of an object 13, for example, a patient who is to be treated and who lies at the isocenter of the gantry rotation. The rotational axis 8 of the gantry 6, the rotational axis 14 of a treatment table 16, and the beam axis 10 intersect in the isocenter.

The plates or leaves of the beam shielding device within the treatment head 4 are substantially impervious to the emitted radiation. The collimator leaves or plates are mounted between the radiation source and the patient in order to delimit the field. Areas of the body, for example, healthy tissue, are therefore subject to as little radiation as possible and preferably to none at all. The plates or leaves are movable such that the distribution of radiation over the field need not be uniform (one region can be given a higher dose than another). As will be explained in greater detail below, the leaves are controllable according to embodiments of the present invention to deliver improved IMRT. Furthermore, the gantry can be rotated so as to allow different beam angles and radiation distributions without having to move the patient.

The radiation treatment device 2 also includes a central treatment processing or control unit 200 which is typically located apart from the radiation treatment device 2. The radiation treatment device 2 is normally located in a different room to protect the therapist from radiation. The treatment unit 200 includes a central processor 18 and includes output devices such as at least one visual display unit or monitor 70 and an input device such as a keyboard 19. Data can be input also through data carriers such as data storage devices or a verification and recording or automatic setup system.

The treatment processing unit 200 is typically operated by the therapist who administers actual delivery of radiation treatment as prescribed by an oncologist by using the keyboard 19 or other input device. The therapist enters into the control unit of the treatment unit 200 the data that defines the radiation dose to be delivered to the patient, for example, according to the prescription of the oncologist. The program can also be input via another input device, such a data storage device. Various data can be displayed before and during the treatment on the screen of the monitor 70.

As will be described in greater detail below, the treatment processing unit 200 is used to determine a dynamic IMRT treatment and control of the beam shielding device according to embodiments of the present invention.

Figure 5:
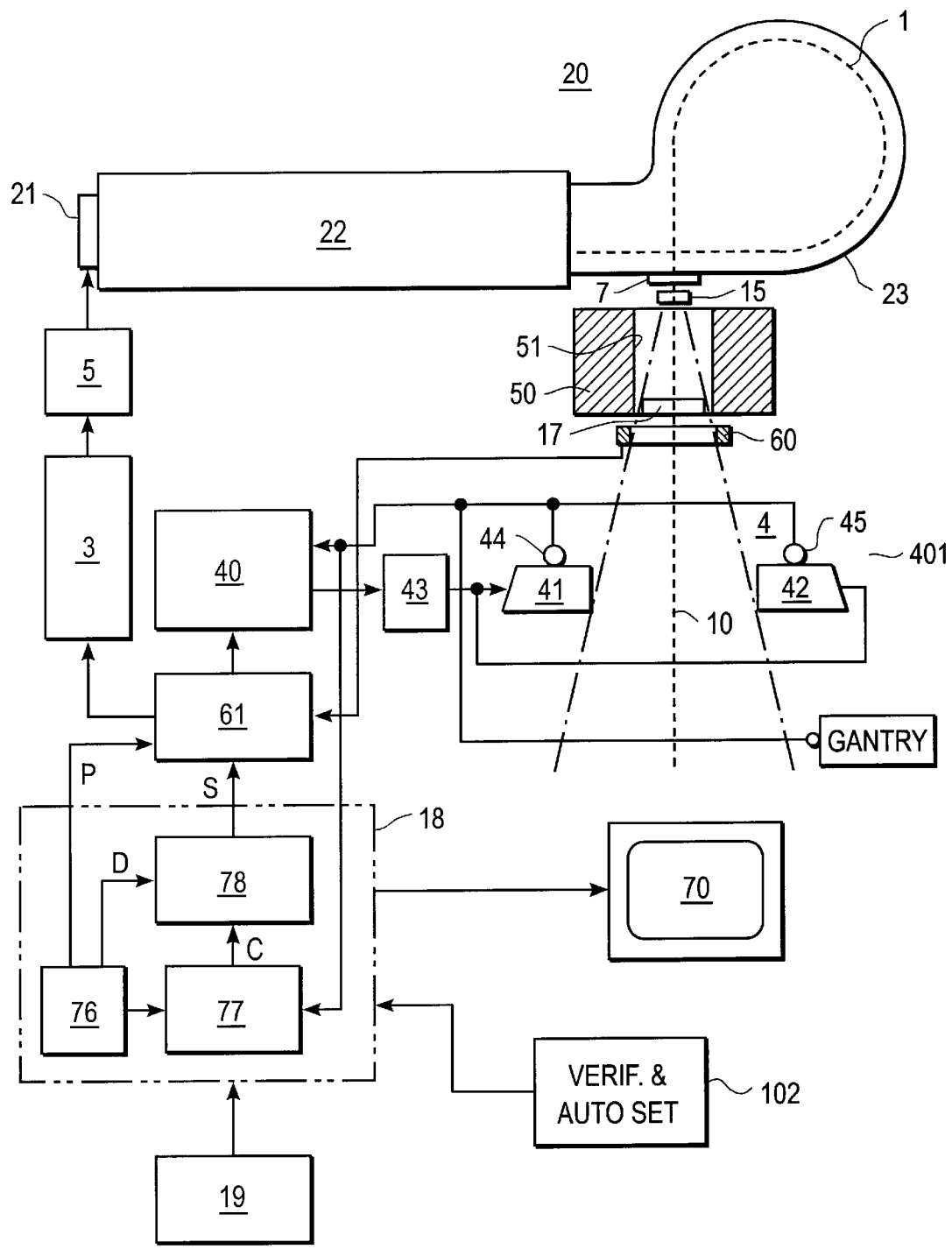
FIG. 5 is a block diagram of a radiation therapy device according to an embodiment of the invention.
Figure 6:
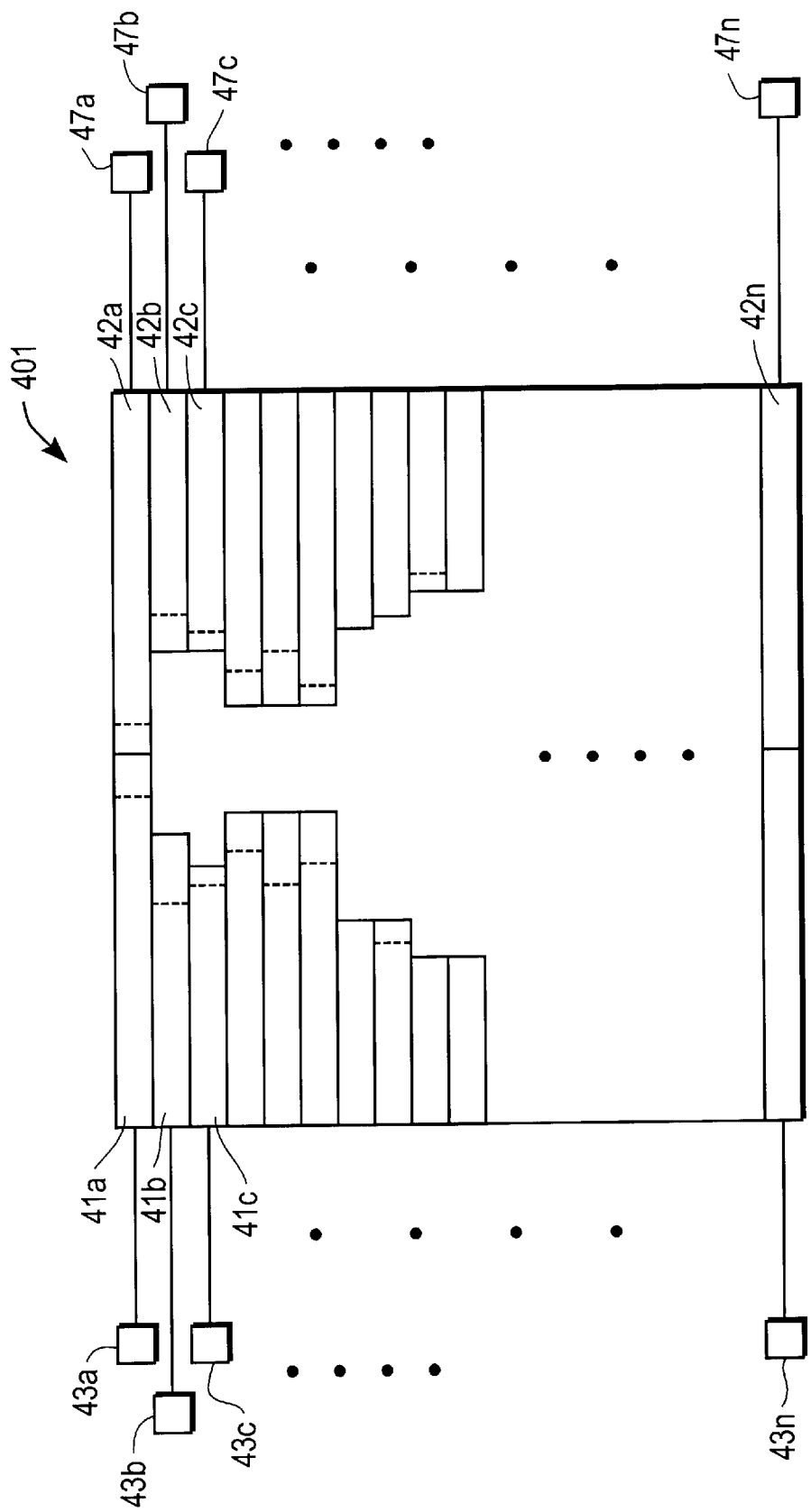
FIG. 6 is a diagram of a multileaf collimator according to an embodiment of the invention.

A block diagram of the radiation treatment device 2 and portions of the treatment unit 200 are, according to the present invention, illustrated in greater detail in FIG. 5. An electron beam 1 is generated in an electron accelerator 20. The electron accelerator 20 includes an electron gun 21, a wave guide 22 and an evacuated envelope or guide magnet 23. A trigger system 3 generates injector trigger signals and supplies them to the injector 5. Based on these injector trigger signals, the injector 5 generates injector pulses which are fed to the electron gun 21 in the accelerator 20 for generating electron beam 1. The electron beam 1 is accelerated and guided by the wave guide 22. For this purpose, a high frequency source 90, such as a magnetron or klystron, is provided, which supplies radio frequency signals for the generation of an electromagnetic field supplied to the waveguide 22. The electrons injected by the injector 5 and emitted by the electron gun 21 are accelerated by this electromagnetic field in the waveguide 22 and exit at the end opposite to electron gun 21 in electron beam 1.

The electron beam 1 enters a guide magnet 23 and from there is guided through a window 7 along axis 10. After passing through a first scattering foil 15, the beam goes through a passageway 51 of a shield block 50 and encounters a flattening filter 17. Next, it is sent through a measuring chamber 60 in which the dose is ascertained. If the scattering foil is replaced by a target, the radiation beam is an X-ray beam; in this case, the flattening filter 17 may be absent, but it is typically present.

Finally, a beam shielding device 401 is provided in the path of radiation beam 1, by which the irradiated field of the subject of investigation is determined. As illustrated, the beam shielding device 401 may include a plurality of opposing plates 41 and 42, only two of which are illustrated for convenience. In one embodiment, additional pairs of plates (not shown) are arranged perpendicular to plates 41 and 42. The plates 41, 42 are moved with respect to axis 10 by a drive unit 43 (which is indicated in FIG. 5 only with respect to plate 41) to change the size of the irradiated field. The drive unit 43 includes an electric motor which is coupled to the plates 41 and 42 and which is controlled by a motor controller 40. Position sensors 44 and 45 are also coupled to the plates 41 and 42, respectively for sensing their positions.

As discussed above, the plate arrangement 401 may alternatively or additionally include a multi-leaf collimator having many radiation blocking leaves. Such a multi-leaf collimator is illustrated in greater detail in FIG. 6. The leaves of such a multi-leaf collimator include a plurality of opposing leaf or rod pairs, each driven by a motor or drive unit 43, 47. The drive units move the leaves in and out of the treatment field, thus creating the desired field shape. The rods, or leaves, are relatively narrow, and cast a shadow of about 0.5 to 1. cm at isocenter.

Returning to FIG. 5, the motor controller 40 is coupled to a dose unit 61 which may include a dosimetry controller 61a according to the present invention and which is coupled to a central processing unit 18 for providing set values for the radiation beam for achieving given isodose curves.

The central processing unit 18 is programmed by the therapist according to the instructions of the oncologist and typically performs an optimization so that the radiation treatment device carries out the prescribed radiation treatment. The delivery of the radiation treatment is input through a keyboard 19. The central processing unit 18 is further coupled to provide set signals to the dose control unit 61 that generates the desired values of radiation for controlling trigger system 3. The trigger system 3 then adapts the pulse radiation frequency and other parameters in a corresponding, conventional manner. The central processing unit 18 further includes a control unit 76 which controls execution of the program and the opening and closing of the collimator plates 41, 42 to deliver radiation according to a desired intensity profile. In addition, a memory 77 and additional combination control circuitry 78 may be provided, as are described in U.S. Pat. No. 5,724,403, which is hereby incorporated by reference in its entirety as if fully set forth herein.

The central processing unit 18 is configured to deliver auto-sequencing of intensity modulated treatments. One or more functional units, such as a verification and auto setup unit 102, provide inputs to the CPU 18 for controlling the radiation treatment. For example, once the verification and auto set-up unit 102 has verified system set-up, a RAD ON enable signal may be provided to the CPU 18. In response, the CPU 18 may issue a RAD ON signal to the trigger system 3 via the dose unit 61. The trigger system 3 then provides the injector and modulator triggers to the injector and modulator, respectively, to generate the applied radiation beam.

As noted above, in an intensity modulated treatment system, the dose absorbed by the object is dependent on the dose, time applied, and the configuration of the beam shielding device. As noted above, a dynamic IMRT scheme according to an embodiment of the invention defines a RAD ON/RAD OFF cycle as an IMRT segment. Every set of opposing leaves in the collimator produces an IMRT profile or track. According to such an embodiment, at least one of the opposing leaves in each track moves toward the other to produce the given track. When a track is complete, the opposing leaves remain together until the end of the segment. The dose rate remains constant during the segment. It is noted that, in certain embodiments, delivery is determined such that the leaves are closed to a predetermined gap (e.g., a few millimeters); the gap is then "filled" with remaining radiation dosage, and the leaves are then closed as quickly as possible.

The basic relationship between leaf velocities, track slopes and the dose rate is given by:

$$Vi = DR\ (MU/\text{sec})/\text{Slope}(MU/\text{mm})$$

The selection of collimator position, leaf velocities, and dose rate may typically be performed based on minimizing treatment time.

Figure 7:
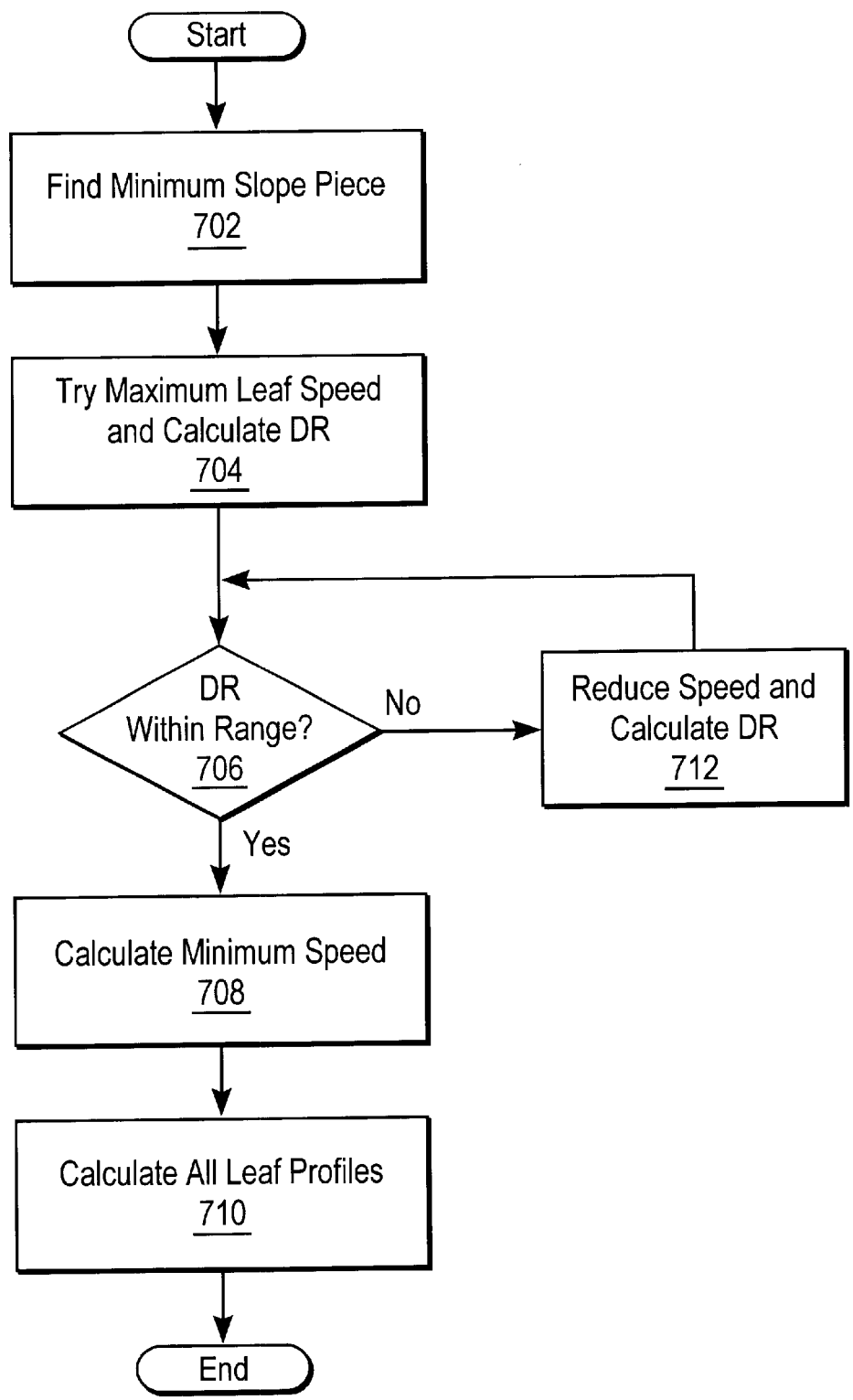
FIG. 7 is a diagram of a flowchart according to an implementation of the invention.

FIG. 7 is a flowchart illustrating a method in accordance with an embodiment of the invention. It is noted that various methods that take into account system dose rate and maximum and minimum leaf speed capabilities could be employed. Thus, FIG. 7 is exemplary only. In particular, the flowchart 700 illustrates a possible mechanism for selecting a leaf velocity profile and constant dose rate for one segment. In a step 702 the minimum slope piece within a given segment is determined, where "slope" is the number of monitor units (MU's) over a particular distance. In a step 704, a maximum possible leaf speed is determined and a dose rate corresponding to that maximum speed is calculated. If the resulting dose rate is within range for the machine, as determined in 706, then the speed corresponding to the maximum slope piece is determined, in 708, to see if it is within range. If the dose rate is outside system range, then in 712 the speed is reduced by a predetermined increment and dose rate is again determined to see if it is within range. Once the dose rate and maximum speed are within range, the minimum speed is calculated in 708. If the minimum speed is within range, then all leaf profiles are calculated in 710.

Figure 1B:
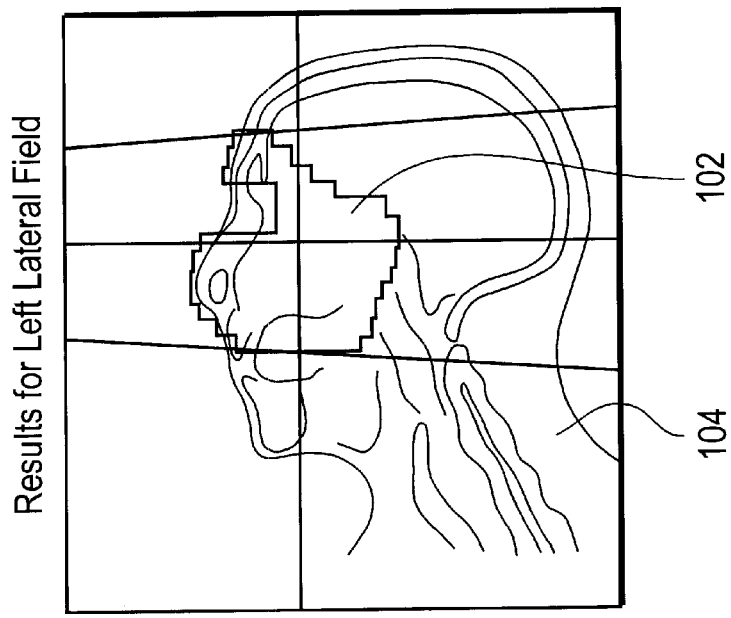
FIG. 1A and FIG. 1B illustrate an intensity map and footprint, respectively.
Figure 1A:
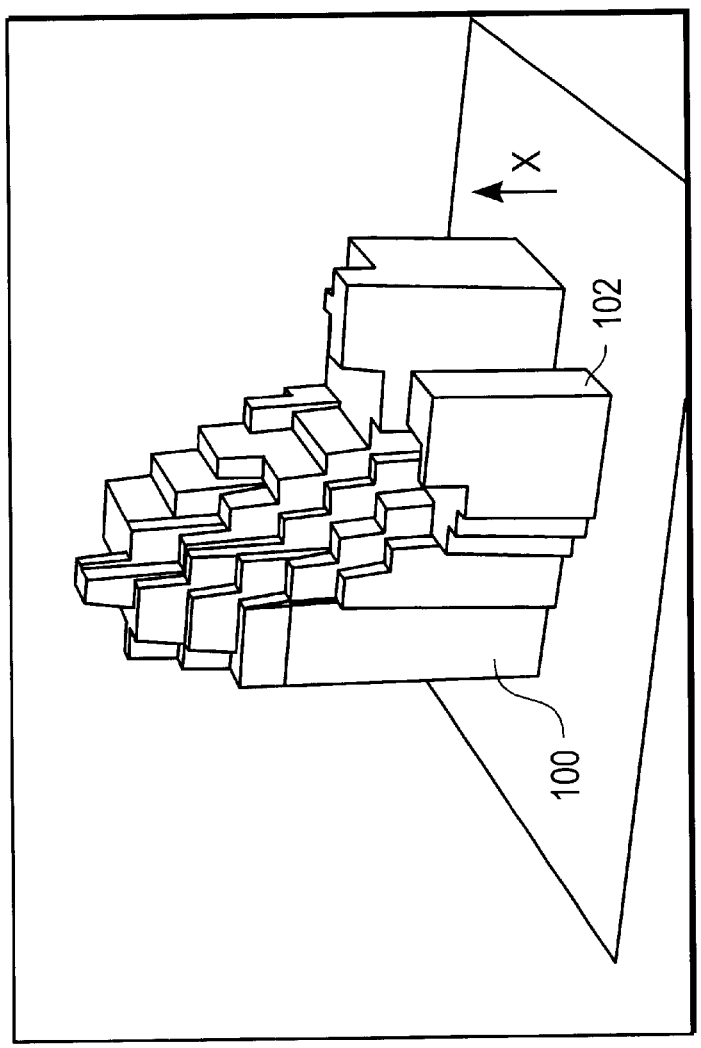
Figure 2B:
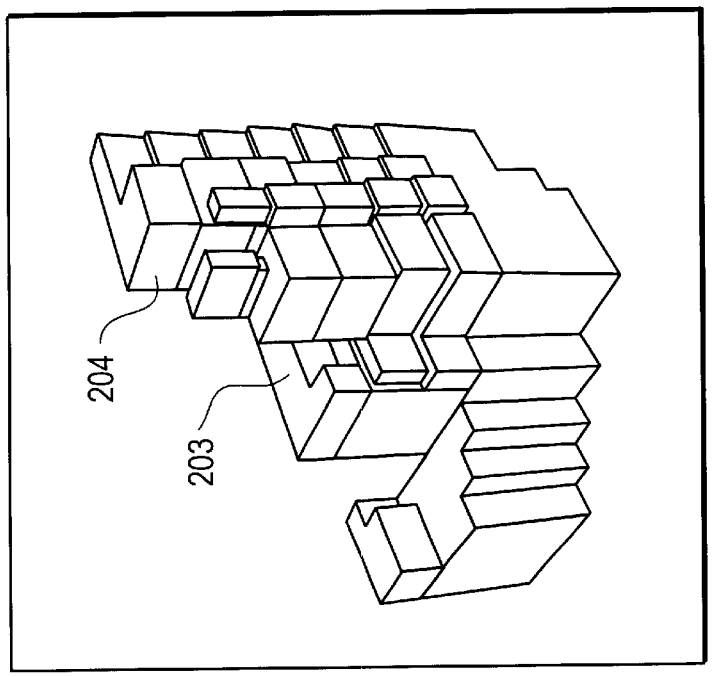
FIG. 2A and FIG. 2B illustrate sequential IMRT.
Figure 2A:
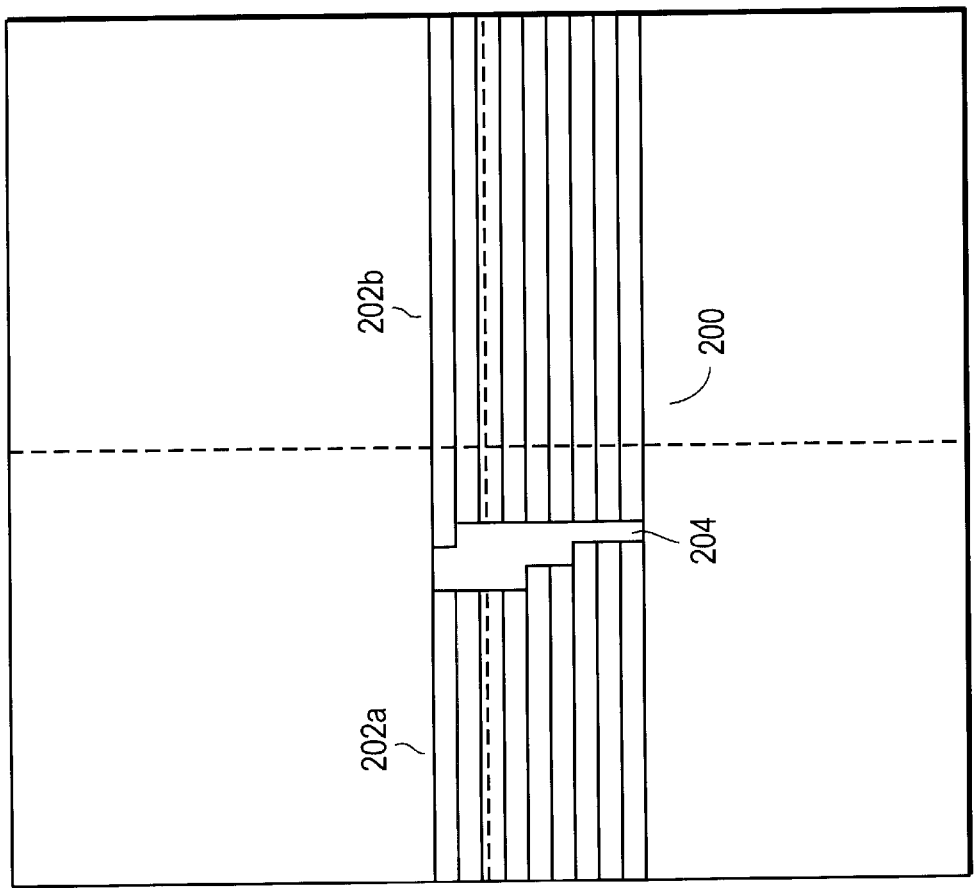
Figure 3:
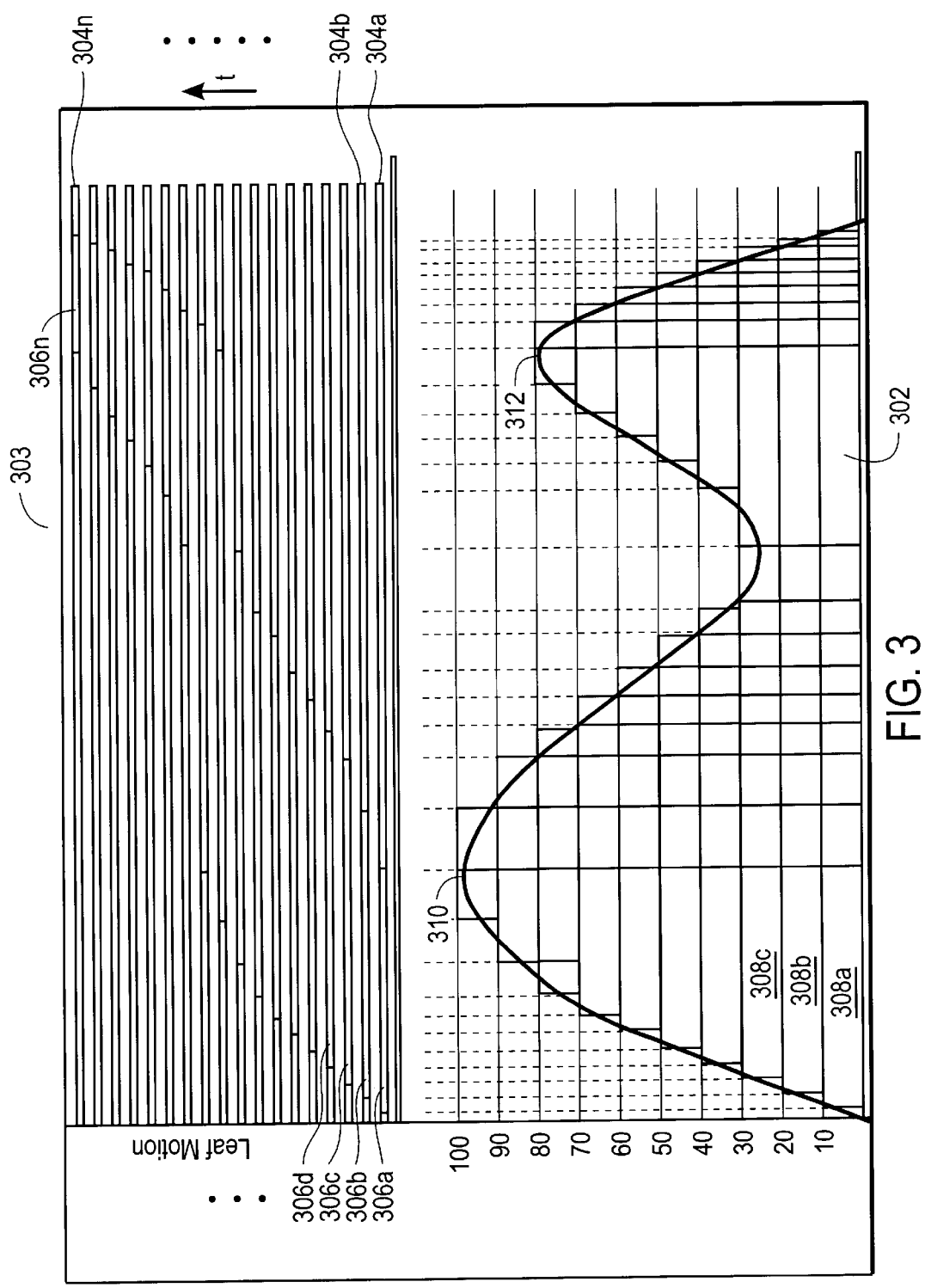
FIG. 3 illustrates sliding window IMRT.

Operation of the present invention is viewed by way of example. FIG. 8A is an intensity map corresponding to the map of FIG. 1A, showing leaf axis, dose axis, and field size.

FIG. 8B is a table of actual values for the intensity map of FIG. 8A. The intensity map has been divided into two IMRT segments 802, 804. The numbers in the boxes represent the dose in monitor units.

In this case, FIG. 9 illustrates a revised intensity map that is to be delivered using the dynamic scheme described herein. The initial 19 MU may be delivered using static (non-moving) leaves at the maximum dose rate for a period of 3.8 seconds. Thus, the values in the map of FIG. 8 have 19 MU subtracted from them. The balance are delivered using dynamic leaves. FIG. 10 illustrates the leaf velocities profile for the first segment delivery. The leaves with arrows <or> indicate movement. The minimum slope is 0.1 MU/mm. The maximum velocity is 20 mm/sec while dose rate is 120 MU/min. The maximum slope is 4 MU/mm and the minimum velocity is 0.5 mm/second. The RAD ON time is 50.5 seconds. The values in the boxes represent the velocity at which the leaf is moving through the box.

FIG. 11 and FIG. 12 illustrate delivery of the second segment. Again, the initial 19 MU are delivered at maximum dose rate with static leaves (3.8 sec) with the balance (values shown in FIG. 11) to be delivered with dynamic leaves. Thus, FIG. 12 is the velocity profile for the second segment. Again, the minimum slope is 0.1 MU/mm. The maximum velocity is 20 mm/sec (120 MU/min). The maximum slope is 4.1 MU/mm and minimum velocity is 49 mm/sec. Rad ON time is 30.5 seconds.

The invention described in the above detailed description is not intended to be limited to the specific form set forth herein, but is intended to cover such alternatives, modifications and equivalents as can reasonably be included within the spirit and scope of the appended claims.

What is claimed is:

1. A method for delivering radiation therapy, comprising:
   defining a RAD on/RAD OFF cycle as an IMRT segment;
   defining sets of opposing leaves as an IMRT profile;
   moving at least one of said opposing leaves toward the other to produce a track;
   maintaining a constant dose rate during the segment; and
   wherein every moving leaf goes from an open position to a closed position.

2. A method according to claim 1, wherein when a track is closed, the opposing leaves remain closed until the end of the segment.

3. A method according to claim 2, wherein selecting a leaf velocity profile and dose rate comprises:
   finding a minimum slope within a given segment;
   selecting a maximum leaf speed and calculating a corresponding dose rate;
   if the dose rate is within range, determining a speed corresponding to a maximum slope and verifying that it is within range;
   if the dose rate is outside the range, reducing the speed a predetermined increment and determining again if the dose rate is within range;
   once dose rate and maximum speed are within range, calculating a minimum speed; and
   if minimum speed is within range, then determining all leaf speed profiles.

4. A radiation therapy device, comprising:
   a linear accelerator;
   a beam shielding device including at least one pair of opposing leaves, said at least one pair defining a track during a treatment segment; and
   a controller adapted to determine a leaf speed profile for a segment such that at least one of said opposing leaves constantly moves toward the other from an open position to a closed position on said track while dose rate remains constant during the segment.

5. A device according to claim 4, said beam shielding device comprising a multi-leaf collimator.

6. A device according to claim 5 wherein, when a track is complete the corresponding leaves remain closed until the end of the segment.

7. A device according to claim 6, said controller is adapted to determine a leaf speed profile by determining a minimum slope;

calculating a dose rate if a maximum leaf speed is used;

determining a speed corresponding to a maximum slope if dose rate is within a predetermined range;

calculating a minimum speed; and calculating all leaf profiles.

8. A radiation therapy device according to claim 6, determining leaf profiles, said leaf profiles constrained by a system minimum and maximum speed and maximum dose rate.

9. A radiation therapy device, comprising:

means for delivering radiation to a body;

a multileaf collimator comprising a plurality of sets of opposing leaves, said sets defining tracks; and a controller operable to control said multileaf collimator and said radiation delivering means such that at least one of the opposing leaves constantly moves toward the other from an open position to a closed position on a track while dose rate remains constant during a segment.

10. A radiation therapy device in accordance with claim 9, wherein when a track is complete the corresponding leaves remain closed until the end of the segment.

11. A controller for a radiation therapy device, the device including a multileaf collimator having a plurality of sets of opposing leaves, the sets defining tracks, the controller adapted to control said device such that at least one of the opposing leaves constantly moves toward the other from an open position to a closed position on a track while dose rate remains constant during a segment.

12. A controller in accordance with claim 11, wherein when a track is complete the corresponding leaves remain closed until the end of the segment.

* * * * *